US012797540B2

(12) United States Patent
Cardinali et al.

(10) Patent No.: US 12,797,540 B2
(45) Date of Patent: Nov. 17, 2026

(54) BLOOD GLUCOSE RATE OF CHANGE MODULATION OF MEAL AND CORRECTION INSULIN BOLUS QUANTITY

(71) Applicant: INSULET CORPORATION, Acton, MA (US)

(72) Inventors: Steven Cardinali, Tewksbury, MA (US); Joon Bok Lee, Acton, MA (US); Jason O'Connor, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 18/474,566

(22) Filed: Sep. 26, 2023

(65) Prior Publication Data

US 2024/0009393 A1 Jan. 11, 2024

Related U.S. Application Data

(62) Division of application No. 16/570,125, filed on Sep. 13, 2019, now Pat. No. 11,801,344.

(51) Int. Cl.

| | |
|---|---|
| ***A61M 5/172*** | (2006.01) |
| ***A61B 5/00*** | (2006.01) |
| ***A61B 5/145*** | (2006.01) |
| ***A61M 5/142*** | (2006.01) |
| ***G16H 10/60*** | (2018.01) |

(Continued)

(52) U.S. Cl.

CPC ....... *A61M 5/1723* (2013.01); *A61B 5/14532* (2013.01); *G16H 10/60* (2018.01); *G16H 20/17* (2018.01); *A61B 5/4839* (2013.01); *A61B 5/683* (2013.01); *A61M 2005/14208* (2013.01); *A61M 5/14244* (2013.01); *A61M 2005/1726* (2013.01);

(Continued)

(58) Field of Classification Search

CPC ........ G16H 20/17; G16H 40/63; G16H 50/20; G16H 50/30; G16H 40/60; G16H 20/10; A61M 5/1723; A61M 2230/201; A61M 2005/14208; A61M 2230/005; A61M 2005/1726; A61B 5/14532; A61B 5/4839; A61B 5/7275

See application file for complete search history.

(56) References Cited

U.S. PATENT DOCUMENTS

| | | | | |
|---|---|---|---|---|
| 11,801,344 B2 * | 10/2023 | Cardinali | ............... | G16H 40/60 |
| 2015/0165117 A1 * | 6/2015 | Palerm | .................... | G16Z 99/00 604/151 |

(Continued)

*Primary Examiner* — Karen E Toth

(74) *Attorney, Agent, or Firm* — Goodwin Procter LLP

(57) ABSTRACT

Disclosed are a system, methods and computer-readable medium products that provide bolus dosage calculations by a control algorithm-based drug delivery system that provides automatic delivery of a drug, such as insulin or the like, based on sensor input. Blood glucose measurement values may be received at regular time intervals from a sensor. Using the blood glucose measurements, the control algorithm may perform various calculations and determinations to provide an appropriate bolus dosage. The appropriate bolus dosage may be used to respond to a trend in a trajectory of blood glucose measurements. In addition, a bolus dosage may also be determined by the disclosed device, system, method and/or computer-readable medium product in response to an indication that a user consumed a meal.

20 Claims, 8 Drawing Sheets

700

(51) Int. Cl.
*G16H 15/00* (2018.01)
*G16H 20/17* (2018.01)

(52) U.S. Cl.
CPC ... *A61M 2205/52* (2013.01); *A61M 2230/201* (2013.01); *G16H 15/00* (2018.01)

(56) References Cited

U.S. PATENT DOCUMENTS

| | | | | |
|---|---|---|---|---|
| 2016/0158438 | A1* | 6/2016 | Monirabbasi | A61M 5/14566 604/67 |
| 2016/0175520 | A1* | 6/2016 | Palerm | A61M 5/16831 604/503 |
| 2018/0200441 | A1* | 7/2018 | Desborough | A61B 5/14532 |
| 2022/0288311 | A1* | 9/2022 | Lee | A61B 5/14532 |
| 2025/0148667 | A1* | 5/2025 | Kamath | A61B 5/0002 |

* cited by examiner

600

700

BLOOD GLUCOSE RATE OF CHANGE MODULATION OF MEAL AND CORRECTION INSULIN BOLUS QUANTITY

RELATED APPLICATIONS

This application is a division of U.S. patent application Ser. No. 16/570,125, filed Sep. 13, 2019, the contents of which are incorporated herein by reference in their entirety.

TECHNICAL FIELD

The described examples provide features for a drug delivery system that accounts for a rate of change in blood glucose measurement values.

BACKGROUND

Drug or therapeutic agent delivery systems typically deliver a drug or therapeutic agent to a user based on health conditions of the user. However, because of the complicated and dynamic nature of the human body's response to insulin, it is not uncommon for patients to end up in a hypoglycemic or hyperglycemic state after providing themselves with a meal or correction bolus. This outcome is undesirable for many reasons: hypoglycemia creates an immediate risk of a severe medical event (seizure, coma, death) while hyperglycemia creates long term negative health effects as well as the risk of ketoacidosis. Whether a patient ends up hypoglycemic, hyperglycemic, or within range after a bolus depends on many things including how fast, and in which direction, your blood glucose is changing. If a patient uses a typical finger stick test to assess blood glucose, they typically do not have the blood glucose rate of change information due to the infrequent nature of the tests. If a patient is wearing a continuous glucose monitor (CGM) they will typically have enough data to have an accurate blood glucose rate of change value. Yet, due to the lag time between 1) the bodies interstitial fluid response to blood glucose changes, 2) the CGM providing a blood glucose value, and 3) a patient using the data to determine an insulin treatment quantity there may be a significant difference between the CGM blood glucose value the patient is using to calculate their insulin treatment and the patient's actual blood glucose. This difference may cause the patient to become hypoglycemic or hyperglycemic after their insulin treatment, depending on the magnitude and direction of the blood glucose rate of change. Of the two scenarios, hypoglycemia is seen to be the less desirable and more dangerous of the two.

Systems are available that apply a percentage increase/decrease to the final insulin amount based on rate of change. These systems assign a bonus (or reduction) percentage, such as plus or minus 30 percent, of insulin based on the patient's blood glucose rate of change. While this has proven to be effective, the blanket adjustment is still not optimal and is not as effective for correction boluses, particularly, correction boluses taken to compensate for consumption of a meal. Therefore, there is a need to provide more effective correction bolus dosages that may result in a reduced amount of time a patient may be in a hypoglycemic state.

SUMMARY

Disclosed is an example of a non-transitory computer readable medium that is embodied with programming code executable by a processor. The processor when executing the programming code is operable to perform functions that include receiving a number of blood glucose measurement values over a period of time. A correction bolus dosage based on a latest blood glucose measurement value of the number of blood glucose measurement values may be calculated. A rate of change of blood glucose values may be determined from the number of blood glucose measurement values over the period of time. A revised bolus dosage using the determined rate of change and the latest blood glucose measurement value may be calculated. A function may be applied to the correction bolus dosage and the revised bolus dosage, and, based on an output from the function, a final insulin value may be determined. An insulin bolus dosage may be set using the determined final insulin value, and delivery of insulin according to the set insulin bolus dosage may be actuated.

Disclosed is a device including a processor, a memory, and a transceiver. The processor when executing the artificial pancreas application is operable to control delivery of insulin, and to perform functions. The functions include obtaining a number of blood glucose measurement values. The processor calculates a correction bolus dosage based on a latest blood glucose measurement value of the number of blood glucose measurement values. A rate of change of blood glucose values from the number of blood glucose measurement values over a period of time may be determined. A revised bolus dosage may be calculated using the determined rate of change and the latest blood glucose measurement value. A function may be applied to the correction bolus dosage and the revised bolus dosage. A final insulin value may be determined based on an output from the function.

Disclosed is a method that includes receiving a number of blood glucose measurement values over a period of time. A processor may determine a correction bolus dosage of insulin is required by a user based on an evaluation of the number of blood glucose measurement values. A final insulin value of the correction bolus dosage may be obtained based on an output of a function. The function utilizes a selected blood glucose measurement value of the number of blood glucose measurement values, a target blood glucose value of the user, and an insulin adjustment factor to generate the output of the function. An insulin bolus dosage may be set based on the obtained final insulin value, and delivery of insulin according to the set insulin bolus dosage may be actuated.

DETAILED DESCRIPTION

Various examples provide a method, a system, a device and a computer-readable medium for reducing risk of hypoglycemia by considering the glucose rate of change. For example, there may be the potential for a delay of several minutes, or tens of minutes, between an individual's actual blood glucose state relative to a blood glucose measurement value output by a CGM and when the patient will administer a bolus injection based on the blood glucose measurement value output by the CGM. In the disclosed examples, the delay between an individual's actual blood glucose state and when the patient bolus may be considered to optimize treatment. For example, a current blood glucose value received from a CGM may be projected forward assuming a constant rate of change for some number of minutes. This projected blood glucose value may be used in the calculation of a bolus determination (both time and amount).

An example provides a process that may be used with any additional algorithms or computer applications that manage blood glucose levels and insulin therapy. Such algorithms may be referred to as an "artificial pancreas" algorithm-based system, or more generally, an artificial pancreas (AP) application, that provides automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. However, an AP application as described herein may be able to establish a target blood glucose value more precisely and may set the target blood glucose value at, for example, 110 mg/dL, or the like. As described in more detail with reference to the examples of FIGS. 1-7, the AP application may utilize the monitored blood glucose values and other information to generate and send a command to a medical device including, for example, a pump, to control delivery of a bolus dose of insulin to the user, change the amount or timing of future doses, as well as to control other functions.

Figure 1:
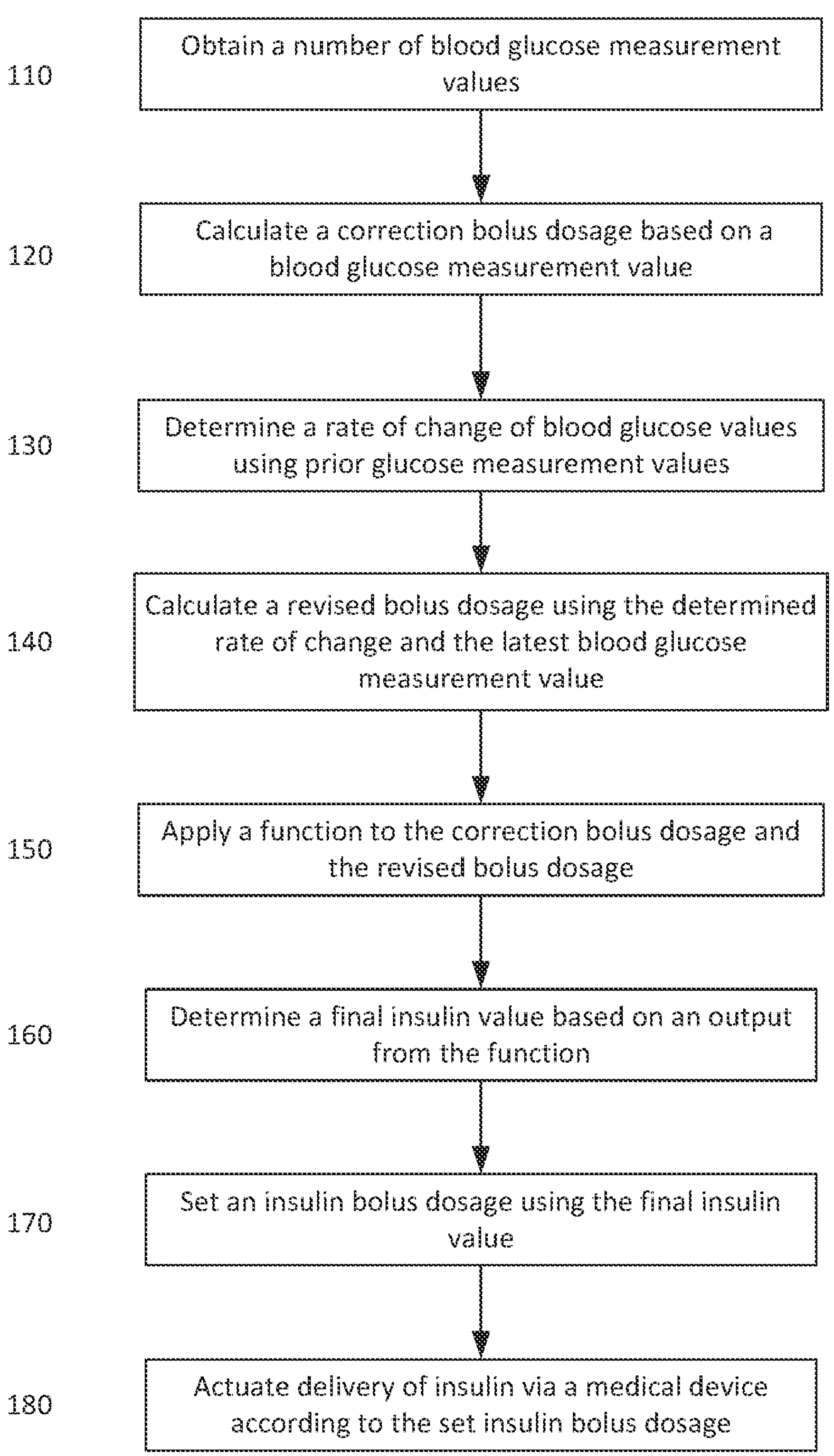
FIG. 1 shows a flow chart of an example process for determining a dosage of a bolus injection for correcting a blood glucose level.

FIG. 1 shows a flow chart of a process for determining a dosage of a bolus injection for correcting a blood glucose level. The process 100 may be implemented by programming code that is executed by a processor. For example, a processor when executing the programming code is operable to perform various functions. The various functions may include obtaining a number of blood glucose measurement values (110). For example, the number of blood glucose measurement values may be received over a period of time from a CGM or another device via a wireless signal (not shown in this example—hardware elements and system elements are described in more detail with reference to the example of FIG. 2). The period of time may be approximately every 5 minutes, every minute, or some other increment of time. In addition, an individual blood glucose measurement value of the number of blood glucose measurement values may be received very shortly, for example, almost instantaneously, after being measured, or may be delivered in a batch of two or more, or the like. The processor may process each of the number of blood glucose measurement values. Based on a blood glucose measurement value of the number of blood glucose measurement values, a correction bolus dosage may be calculated (120). For example, the blood glucose measurement value of the number of blood glucose measurement values used to calculate the correction bolus dosage may be a latest blood glucose measurement value. In this example, the latest blood glucose measurement value is the last blood glucose measurement value received by the processor may be the latest blood glucose measurement value. Alternatively, any of the number of blood glucose measurement values may be selected for use in the calculation of the correction bolus dosage.

$$\text{Correction Bolus Dosage} = \left(\frac{CGM - \text{target}}{ISF}\right) * IAF \qquad \text{Eq. 1}$$

A correction bolus dosage, as shown in Equation (Eq.) 1, may be calculated by determining a difference between the latest (or a selected) blood glucose measurement value and a target blood glucose value. The target blood glucose value may be considered the standard of care for a particular patient, standard of care for a large population of diabetics, or the desired glucose concentration preference for a particular patient. In some examples, in order to account for a particular user's capability to process insulin, an insulin sensitivity factor (ISF) may be applied (e.g. through multiplication, subtraction, division and/or other mathematical operation) to the determined difference to provide a personalized insulin value. In Eq. 1, ISF is a divisor of the difference between the latest blood glucose measurement value and a target blood glucose value and may be considered a parameter indicative of how much a user's measured blood glucose value drops per unit of insulin. In an example, ISF may be personalized for each user and is calculated from clinical values of the respective user determined based on user's diabetes (or other illness) treatment plan.

The personalized insulin value (i.e., ((CGM–target)/ISF)) may be further modified by applying an insulin adjustment factor (IAF) to the personalized insulin value to generate the correction bolus dosage. In an example, the range of values for IAF may be from approximately 0.30 to approximately 0.70. Of course, other ranges for the IAF may be used, such as 0.25-0.65, or the like. In some examples, the correction bolus dosage may be constrained at the upper boundary by a recommended bolus dosage modified by the IAF proportional to a trajectory of the number of blood glucose measurement values and another constraint may be that the recommended bolus is not more than is required to get the target blood glucose if the blood glucose trajectory is substantially constant for approximately 25 minutes (i.e., 5 cycles of blood glucose measurements by a CGM).

A rate of change (RoC) of blood glucose values may be determined from the number of blood glucose measurement values over the period of time (130). For example, the rate of change of the blood glucose measurement values may be derived from the slope. In other examples, a function fitted to a plot of each respective blood glucose measurement value over time may be determined and used to determine a rate of change. Alternatively, the rate of change of blood glucose value may be directly measured by a CGM.

At 140, the processor may use the determined rate of change and the latest blood glucose measurement value to calculate a revised bolus dosage. The rate of change may be multiplied by a time parameter to that will be used determine a modified latest blood glucose measurement value. For example, the processor may access a table of time parameters stored in memory. A time parameter may be selected from the table based on a predicted user response time to a dose of insulin, such as one unit of insulin, two units of insulin, or the like. The time parameter may be applied (e.g., as a multiplier) to the determined rate of change to generate a projected blood glucose measurement value (i.e., (RoC)×T=projected blood glucose measurement value). The latest blood glucose measurement value may be obtained by the processor using a latest blood glucose measurement and the projected blood glucose measurement value. For example, the processor may obtain the latest blood glucose measurement value from a memory coupled to the processor, a CGM, or via another external device, such as smart accessory device. The projected blood glucose measurement value may be added to the latest blood glucose measurement (CGM) value (e.g., CGM+(RoC)×T) to obtain a modified latest blood glucose measurement value. The time parameter T may be in minutes, such as 5 minutes, 15 minutes, 16 minutes, 25 minutes, or the like. The processor may retrieve a target blood glucose value (i.e., Target) of the user from a memory coupled to the processor. The difference between the target blood glucose value and the modified latest blood glucose measurement value may be determined. An insulin sensitivity factor (ISF) may be applied (as a divisor or fractional multiplier) to the determined difference to produce a revised bolus dosage as shown in the equation (Eq. 2) below, which may be implemented in programming code.

$$\text{Revised Bolus Dosage} = \frac{(CGM + RoC \times T) - \text{Target}}{ISF} \quad \text{Eq. 2}$$

A function may be applied to the correction bolus dosage and the revised bolus dosage (150). The function may be, for example, a minimum function that is operable to find a minimum value of the inputs to the function as shown in equation 3 (Eq. 3).

$$\text{output}=\min(\text{correction bolus dosage},\text{revised bolus dosage}) \quad \text{Eq. 3}$$

In this example, the inputs to the minimum function may be the correction bolus dosage and the revised bolus dosage, and, at 160, an output from the function, such as that shown in Eq. 3, may be used to determine a final insulin value. The final insulin value may be a volume of insulin, an amount of insulin (in units of insulin), or the like.

The processor may determine the final insulin value and perform further processing. For example, the determined final insulin value may be used to set an insulin bolus dosage (170). In response to setting the insulin bolus dosage, the processor may actuate delivery of insulin according to the set insulin bolus dosage (180). As described with respect to a further example, the processor may actuate delivery of insulin according to the set insulin bolus dosage, for example, by outputting a signal indicating the set insulin bolus dosage to be received by a pump mechanism. The pump mechanism, in response to the received signal, may operate to deliver a bolus dosage according to the set insulin bolus dosage.

Figure 2:
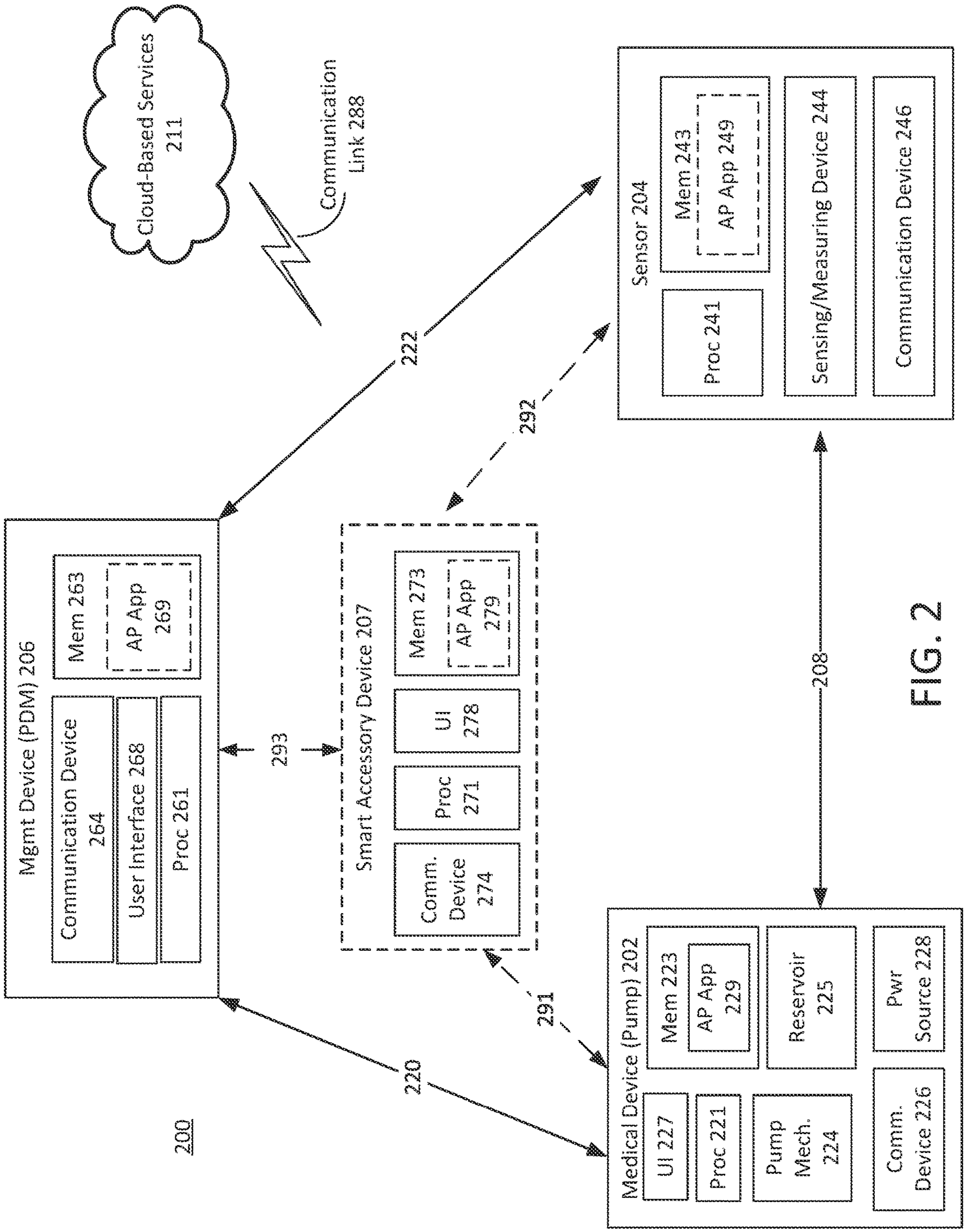
FIG. 2 illustrates a functional block diagram of drug delivery system suitable for implementing the example processes and techniques described herein.

It may be helpful to discuss an example of a drug delivery system that may implement the process example of FIG. 1. FIG. 2 illustrates an example of a drug delivery system 200.

The drug delivery system 200 may be operable to implement an AP application that includes functionality to determine a bolus dosage, output an indication of the determined bolus dosage to actuate delivery of the bolus of insulin based on the indication of the determined bolus dosage. The drug delivery system 200 may be an automated drug delivery system that may include a medical device (pump) 202, a sensor 204, and a management device (PDM) 206. The system 200, in an example, may also include a smart accessory device 207, which may communicate with the other components of system 200 either via a wired or wireless communication link.

In an example, the medical device 202 may be attached to the body of a user, such as a patient or diabetic, and may deliver any therapeutic agent, including any drug or medicine, such as insulin or the like, to a user. The medical device 202 may, for example, be a wearable device worn by the user. For example, the medical device 202 may be directly coupled to a user (e.g., directly attached to a body part and/or skin of the user via an adhesive or the like). In an example, a surface of the medical device 202 may include an adhesive to facilitate attachment to a user.

The medical device 202 may include a number of components to facilitate automated delivery of a drug (also referred to as a therapeutic agent) to the user. The medical device 202 may be operable to store the drug and to provide the drug to the user. The medical device 202 is often referred to as a pump, or an insulin pump, in reference to the operation of expelling a drug from the reservoir 225 for delivery to the user. While the examples refer to the reservoir 225 storing insulin, the reservoir 225 may be operable to store other drugs or therapeutic agents, such as morphine or the like, suitable for automated delivery.

In various examples, the medical device 202 may be an automated, wearable insulin delivery device. For example, the medical device 202 may include a reservoir 225 for storing the drug (such as insulin), a needle or cannula (not shown) for delivering the drug into the body of the user (which may be done subcutaneously, intraperitoneally, or intravenously), and a pump mechanism (mech.) 224, or other drive mechanism, for transferring the drug from the reservoir 225, through a needle or cannula (not shown), and into the user. The pump mechanism 224 may be fluidly coupled to reservoir 225, and communicatively coupled to the processor 221. The medical device 202 may also include a power source 228, such as a battery, a piezoelectric device, or the like, for supplying electrical power to the pump mechanism 224 and/or other components (such as the processor 221, memory 223, and the communication device 226) of the medical device 202. Although not shown, an electrical power supply for supplying electrical power may similarly be included in each of the sensor 204, the smart accessory device 207 and the management device (PDM) 206.

The blood glucose sensor 204 may be a device communicatively coupled to the processor 261 or 221 and may be operable to measure a blood glucose value at a predetermined time interval, such as every 5 minutes, or the like. The blood glucose sensor 204 may provide a number of blood glucose measurement values to the AP applications operating on the respective devices.

The medical device 202 may provide insulin the stored in reservoir 225 to the user based on information (e.g., blood glucose measurement values) provided by the sensor 204 and/or the management device (PDM) 206. For example, the medical device 202 may contain analog and/or digital circuitry that may be implemented as a processor 221 (or controller) for controlling the delivery of the drug or therapeutic agent. The circuitry used to implement the processor 221 may include discrete, specialized logic and/or components, an application-specific integrated circuit, a microcontroller or processor that executes software instructions, firmware, programming instructions or programming code (enabling, for example, the artificial pancreas application (AP App) 229 as well as the process examples of FIGS. 1 and 3) stored in memory 223, or any combination thereof. For example, the processor 221 may execute a control algorithm, such as an artificial pancreas application 229, and other programming code that may make the processor 221 operable to cause the pump to deliver doses of the drug or therapeutic agent to a user at predetermined intervals or as needed to bring blood glucose measurement values to a target blood glucose value. The size and/or timing of the doses may be programmed, for example, into an artificial pancreas application 229 by the user or by a third party (such as a health care provider, medical device manufacturer, or the like) using a wired or wireless link, such as 220, between the medical device 202 and a management device 206 or other device, such as a computing device at a healthcare provider facility. In an example, the pump or medical device 202 is communicatively coupled to the processor 261 of the management device via the wireless link 220 or via a wireless link, such as 291 from smart accessory device 207 or 208 from the sensor 204. The pump mechanism 224 of the medical device may be operable to receive an actuation signal from the processor 261, and in response to receiving the actuation signal, expel insulin from the reservoir 225 according to the set insulin bolus dosage.

The other devices in the system 200, such as management device 206, smart accessory device 207 and sensor 204, may also be operable to perform various functions including controlling the medical device 202. For example, the management device 206 may include a communication device 264, a processor 261, and a management device memory 263. The management device memory 263 may store an instance of the AP application 269 that includes programming code, that when executed by the processor 261 provides the process examples described with reference to the examples of FIGS. 1 and 3. The management device memory 263 may also store programming code for providing the process examples described with reference to the examples of FIGS. 1 and 3-7.

The smart accessory device 207 may be, for example, an Apple Watch®, other wearable smart device, including eyeglasses, provided by other manufacturers, a global positioning system-enabled wearable, a wearable fitness device, smart clothing, or the like. Similar to the management device 206, the smart accessory device 207 may also be operable to perform various functions including controlling the medical device 202. For example, the smart accessory device 207 may include a communication device 274, a processor 271, and a memory 273. The memory 273 may store an instance of the AP application 279 that includes programming code for providing the process examples described with reference to the examples of FIGS. 1 and 3-7. The memory 273 may also as store programming code and be operable to store data related to the AP application 279. The sensor 204 of system 200 may be a continuous glucose monitor (CGM) as described above, that may include a processor 241, a memory 243, a sensing or measuring device 244, and a communication device 246. The memory 243 may store an instance of an AP application 249 as well as other programming code and be operable to store data related to the AP application 249. The AP application 249 may also include programming code for providing the process examples described with reference to the examples of FIGS. 1 and 3-7.

Instructions for determining the delivery of the drug or therapeutic agent (e.g., as a bolus dosage) to the user (e.g., the size and/or timing of any doses of the drug or therapeutic agent) may originate locally by the medical device 202 or may originate remotely and be provided to the medical device 202. In an example of a local determination of drug or therapeutic agent delivery, programming instructions, such as an instance of the artificial pancreas application 229, stored in the memory 223 that is coupled to the medical device 202 may be used to make determinations by the medical device 202. In addition, the medical device 202 may be operable to communicate with the cloud-based services 211 via the communication device 226 and the communication link 288.

Alternatively, the remote instructions may be provided to the medical device 202 over a wired or wireless link by the management device (PDM) 206, which has a processor 261 that executes an instance of the artificial pancreas application 269, or the smart accessory device 207, which has a processor 271 that executes an instance of the artificial pancreas application 269 as well as other programming code for controlling various devices, such as the medical device 202, smart accessory device 207 and/or sensor 204. The medical device 202 may execute any received instructions (originating internally or from the management device 206) for the delivery of the drug or therapeutic agent to the user. In this way, the delivery of the drug or therapeutic agent to a user may be automated.

In various examples, the medical device 202 may communicate via a wireless link 220 with the management device 206. The management device 206 may be an electronic device such as, for example, a smart phone, a tablet, a dedicated diabetes therapy management device, or the like. The management device 206 may be a wearable wireless accessory device. The wireless links 208, 220, 222, 291, 292 and 293 may be any type of wireless link provided by any known wireless standard. As an example, the wireless links 208, 220, 222, 291, 292 and 293 may enable communications between the medical device 202, the management device 206 and sensor 204 based on, for example, Bluetooth®, Wi-Fi®, a near-field communication standard, a cellular standard, or any other wireless optical or radio-frequency protocol.

The sensor 204 may be a glucose sensor operable to measure blood glucose and output a blood glucose value or data that is representative of a blood glucose value. For example, the sensor 204 may be a glucose monitor or a continuous glucose monitor (CGM). The sensor 204 may include a processor 241, a memory 243, a sensing/measuring device 244, and communication device 246. The communication device 246 of sensor 204 may include one or more sensing elements, an electronic transmitter, receiver, and/or transceiver for communicating with the management device 206 over a wireless link 222 or with medical device 202 over the link 208. The sensing/measuring device 244 may include one or more sensing elements, such as a glucose measurement, heart rate monitor, or the like. The processor 241 may include discrete, specialized logic and/or components, an application-specific integrated circuit, a microcontroller or processor that executes software instructions, firmware, programming instructions stored in memory (such as memory 243), or any combination thereof. For example, the memory 243 may store an instance of an AP application 249 that is executable by the processor 241.

Although the sensor 204 is depicted as separate from the medical device 202, in various examples, the sensor 204 and medical device 202 may be incorporated into the same unit. That is, in various examples, the sensor 204 may be a part of the medical device 202 and contained within the same housing of the medical device 202 (e.g., the sensor 204 may be positioned within or embedded within the medical device 202). Glucose monitoring data (e.g., measured blood glucose values) determined by the sensor 204 may be provided to the medical device 202, smart accessory device 207 and/or the management device 206 and may be used to determine a bolus dosage of insulin for automated delivery of insulin by the medical device 202.

The sensor 204 may also be coupled to the user by, for example, adhesive or the like and may provide information or data on one or more medical conditions and/or physical attributes of the user. The information or data provided by the sensor 204 may be used to adjust drug delivery operations of the medical device 202.

In an example, the management device 206 may be a personal diabetes manager. The management device 206 may be used to program or adjust operation of the medical device 202 and/or the sensor 204. The management device 206 may be any portable electronic device including, for example, a dedicated controller, such as processor 261, a smartphone, or a tablet. In an example, the management device (PDM) 206 may include a processor 261, a management device management device memory 263, and a communication device 264. The management device 206 may contain analog and/or digital circuitry that may be implemented as a processor 261 (or controller) for executing processes to manage a user's blood glucose levels and for controlling the delivery of the drug or therapeutic agent to the user. The processor 261 may also be operable to execute programming code stored in the management device management device memory 263. For example, the management device management device memory 263 may be operable to store an artificial pancreas application 269 that may be executed by the processor 261. The processor 261 may when executing the artificial pancreas application 269 may be operable to perform various functions, such as those described with respect to the examples in FIGS. 1 and 3. The communication device 264 may be a receiver, a transmitter, or a transceiver that operates according to one or more radio-frequency protocols. For example, the communication device 264 may include a cellular transceiver and a Bluetooth transceiver that enables the management device 206 to communicate with a data network via the cellular transceiver and with the sensor 204 and the medical device 202. The respective transceivers of communication device 264 may be operable to transmit signals containing information useable by or generated by the AP application or the like. The communication devices 226, 246 and 276 of respective medical device 202, sensor 204 and smart accessory device 207 may also be operable to transmit signals containing information useable by or generated by the AP application or the like.

The medical device 202 may communicate with the sensor 204 over a wireless link 208 and may communicate with the management device 206 over a wireless link 220. The sensor 204 and the management device 206 may communicate over a wireless link 222. The smart accessory device 207, when present, may communicate with the medical device 202, the sensor 204 and the management device 206 over wireless links 291, 292 and 293, respectively. The wireless links 208, 220, 222, 291, 292 and 293 may be any type of wireless link operating using known wireless standards or proprietary standards. As an example, the wireless links 208, 220, 222, 291, 292 and 293 may provide communication links based on Bluetooth®, Wi-Fi, a near-field communication standard, a cellular standard, or any other wireless protocol via the respective communication devices 226, 246 and 264. In some examples, the medical device 202 and/or the management device 206 may include a user interface 227 and 268, respectively, such as a keypad, a touchscreen display, levers, buttons, a microphone, a speaker, a display, or the like, that is operable to allow a user to enter information and allow the management device to output information for presentation to the user.

In various examples, the drug delivery system 200 may be an insulin drug delivery system. In various examples, the medical device 202 may be the OmniPod® (Insulet Corporation, Billerica, MA) insulin delivery device as described in U.S. Pat. Nos. 7,303,549, 7,137,964, or U.S. Pat. No. 6,740,059, each of which is incorporated herein by reference in its entirety.

In various examples, the drug delivery system 200 may implement the artificial pancreas (AP) algorithm (and/or provide AP functionality) to govern or control automated delivery of insulin to a user (e.g., to maintain euglycemia—a normal level of glucose in the blood). The AP application may be implemented by the medical device 202 and/or the sensor 204. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 204). For example, the AP application may determine an appropriate delivery of insulin based on glucose level monitoring of the user through the sensor 204. The AP application may also allow the user to adjust insulin delivery. For example, the AP application may allow the user to issue (e.g., via an input) commands to the medical device 202, such as a command to deliver an insulin bolus. In some examples, different functions of the AP application may be distributed among two or more of the management device 206, the medical device (pump) 202 or the sensor 204. In other examples, the different functions of the AP application may be performed by one device, such the management device 206, the medical device (pump) 202 or the sensor 204. In various examples, the drug delivery system 200 may operate according to or may include features or functionalities of the drug delivery systems described in U.S. patent application Ser. No. 15/359,187, filed Nov. 22, 2016, which is incorporated herein by reference in its entirety.

As described herein, the drug delivery system 200 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 200 or any constituent component thereof (e.g., the medical device 202 and/or the management device 206). The drug delivery system 200—for example, as an insulin delivery system implementing an AP application—may be considered to be a drug delivery system or an AP application-based delivery system that uses sensor inputs (e.g., data collected by the sensor 204).

In an example, one or more of the devices, 202, 204, 206 or 207 may be operable to communicate via a wireless communication link 288 with cloud-based services 211. The cloud-based services 211 may utilize servers and data storage (not shown). The communication link 288 may be a cellular link, a Wi-Fi link, a Bluetooth link, or a combination thereof, that is established between the respective devices 202, 204, 206 or 207 of system 200. The data storage provided by the cloud-based services 211 may store anonymized data, such as user weight, blood glucose measurements, age, meal carbohydrate information, or the like. In addition, the cloud-based services 211 may process the anonymized data from multiple users to provide generalized information related to the various parameters used by the AP application. For example, an age-based general target blood glucose value may be derived from the anonymized data, which may be helpful when a user first begins using a system such as 200. The cloud-based services 211 may also provide processing services for the system 200, such as performing the process 100 in the example of FIG. 2 or additional processes, such as that described below with reference to FIG. 3.

In an example, the device 202 includes a communication device 264, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 211. For example, outputs from the sensor 204 or the medical device (pump) 202 may be transmitted to the cloud-based services 211 for storage or processing via the transceivers of communication device 264. Similarly, medical device 202, management device 206 and sensor 204 may be operable to communicate with the cloud-based services 211 via the communication link 288.

In an example, the respective receiver or transceiver of each respective device, 202, 206 or 207, may be operable to receive signals containing respective blood glucose measurement values of the number of blood glucose measurement values that may be transmitted by the sensor 204. The respective processor of each respective device 202, 206 or 207 may be operable to store each of the respective blood glucose measurement values in a respective memory, such as 223, 263 or 273. The respective blood glucose measurement values may be stored as data related to the artificial pancreas algorithm, such as 229, 249, 269 or 279. In a further example, the AP application operating on any of the management device 206, the smart accessory device 207, or sensor 204 may be operable to transmit, via a transceiver implemented by a respective communication device, 264, 274, 246, a control signal for receipt by a medical device. In the example, the control signal may indicate an amount of insulin to be expelled by the medical device 202.

Figure 3:
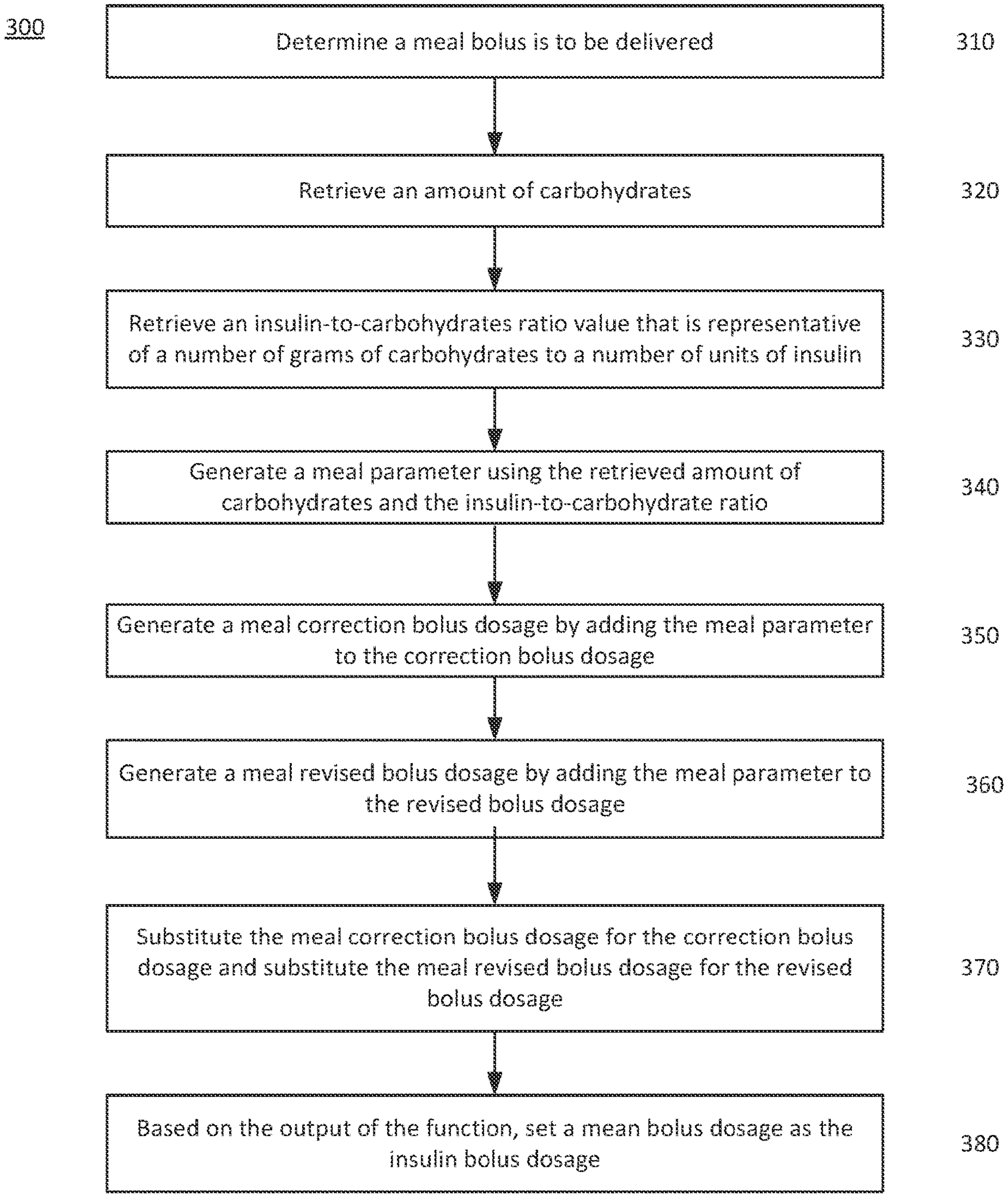
FIG. 3 illustrates a flow chart of an example process for determining a bolus dosage that is to be administered in response to consumption of a meal.

Various operational scenarios and examples of processes performed by the system 200 are described herein. For example, the system 200 may be operable to implement the process example of FIG. 1. In addition, the system 200 may be operable to implement a process that accounts for a meal correction bolus. FIG. 3 illustrates a process example for determining a dosage of a meal correction bolus. The process 300 may be considered a specific implementation of the process 100 of FIG. 1 for use when a meal is consumed, and a meal correction bolus is to be administered to the user. In the example process 300, a processor, such as 221 or 261 of the example in FIG. 2, may be operable to execute programming code to perform the different functions including a determination of whether an indication of a meal bolus is to be output, or an indication of a correction bolus is to be output. The process 300 is similar to the process 100 but with an added parameter that accounts for an amount of carbohydrates consumed by a user and the user's insulin-to-carbohydrate ratio value. In the process 300, a processor, such as 221 or 261, may determine, at 310, that a meal bolus is to be delivered. The consumption of carbohydrates by a user acts to raise the level of glucose in the user's blood. A meal bolus may be delivered to counteract the effects of the ingestion of carbohydrates. For example, a user may be about to ingest or may have finished, a meal and may provide an input via a user interface, such as 268, 227 or 278 to either the PDM 206, medical device 202 or the smart accessory device 278 of FIG. 2 indicating the impending or completed meal. Indications of the impending or completed meal may be used to determine that a meal bolus is to be delivered. For example, a processor may receive information indicating that a meal bolus may be needed, such as a meal bolus request input from a user, a scheduled meal time, a calendar message, a GPS/Wi-Fi location determination, or the like. Typically, when a meal is consumed a meal bolus is administered to counteract the effects of the additional carbohydrates.

At 320, in response to determining a meal bolus is to be delivered, an amount of carbohydrates may be retrieved. The amount of carbohydrates may be an expected amount (a value provided before eating) of carbohydrates to be consumed, an actual amount of carbohydrates consumed (from a nutrition label on a package, or the like), an estimated amount (a value provided after eating) of carbohydrates consumed, or the like, that are input into the system 200 by a user or someone else familiar (e.g., a dietician, a healthcare provider) with the meal being consumed by the user. The amount of carbohydrates may also be received from the cloud-based services 211 in response to a list of foods and approximate portion sizes input by a user, a name of a meal provided by a restaurant that participates with services provided by the cloud-based services 211, or the like.

At 330, the processor may retrieve an insulin-to-carbohydrates ratio (ICR) value that is representative of a number of grams of carbohydrates to a number of units of insulin (e.g., grams per unit of insulin). The ICR value may be stored in a memory, such as 223, 243, 263 or 273 of the respective devices 202, 204, 206 and 207 of FIG. 2. The ICR may be updated according to a setting in the AP application. For example, the ICR may be updated with each measurement of blood glucose reported by the sensor 204 to the AP application or may be updated daily using a number of blood glucose measurements by a respective processor executing the AP application in any one of medical device 202, management device 206 or smart accessory device 207. The AP application may use the retrieved amount of carbohydrates and the insulin-to-carbohydrate ratio value to generate a meal parameter (340). For example, the AP application may be operable to calculate the meal parameter using an equation such as an amount of carbohydrates (CHO) in grams, for example, divided by the ICR to arrive at a meal parameter having a number of units of insulin as a value.

The AP application executed by the processor, at 350, may generate a meal correction bolus dosage for output by an insulin pump device, such as the medical device 202 of FIG. 2, by determining the difference of the blood glucose measurement value from the CGM and the target blood glucose value divided by the ISF, summing the meal parameter and the difference, and multiplying the sum of the meal parameter and the difference with an IAF for the user as shown in Equation 4 below.

$$\text{Meal Correction Bolus Dosage} = \left(\left(\frac{CHO}{ICR}\right) + \frac{(CGM - \text{Target})}{ISF}\right) * IAF \quad \text{Eq. 4}$$

The AP application executed by the processor may generate a meal revised bolus dosage by adding the meal parameter to the revised bolus dosage (360). For example, the AP application executed by the processor may generate a meal revised bolus dosage for output by an insulin pump device, such as the medical device 202 of FIG. 2, by adding the meal parameter to the correction bolus dosage (as described above with reference to FIG. 1) as shown in Equation 5 below.

$$\text{Meal Revised Bolus Dosage} = \left(\frac{CHO}{ICR}\right) + \frac{(CGM + RoC * T - \text{Target})}{ISF} \quad \text{Eq. 5}$$

The function in the process 100, step 150, is applied to determine a meal bolus dosage, except the meal correction bolus dosage may be substituted for the correction bolus dosage and the meal revised bolus dosage may be substituted for the revised bolus dosage to determine a minimum value as shown in Eq. 6 below (370).

Output=min(meal correction bolus dosage,meal revised bolus dosage) Eq. 6

Based on the meal bolus dosage output from the function in Eq. 6, the insulin bolus dosage set equal to the meal bolus dosage (380). In response to control signals generated according the set insulin bolus dosage by an AP application, an insulin bolus may be administered by the medical device 202 to a user.

In the foregoing examples, the bolus dosage calculations for either a correction bolus or a meal correction bolus are described as be included with the programming code of the AP application. However, the foregoing examples may be implemented as add-on programing for use in applications offered by different service providers that deliver functions similar to the AP application described herein.

Figure 4:
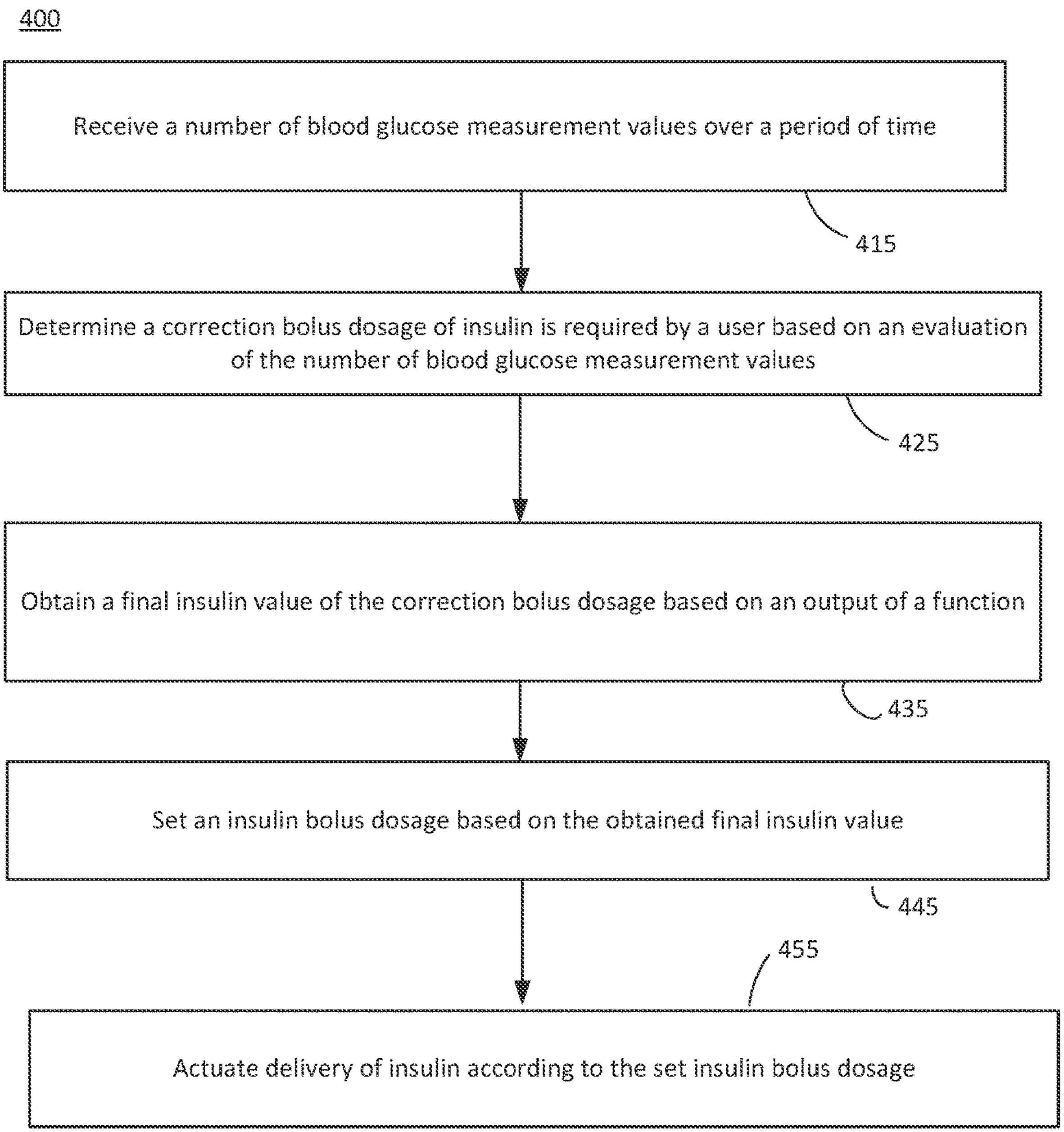
FIG. 4 illustrates a flow chart of another example of a process for determining a dosage of a bolus injection for correcting a blood glucose value.

Additional methods of calculating an insulin bolus are also disclosed. For example, processes that include specific modifications to a generalized process are disclosed. An example of a generalized process is shown in FIG. 4. The process 400 of FIG. 4 includes, at 415 receiving a number of blood glucose measurement values over a period of time. As mentioned, the number of blood glucose measurement values may be made by a CGM over a period of time. For example, a sensor, such as 204, may measure a user's blood glucose every 5 minutes for several days (e.g., until the sensor's power supply is depleted) and provide the results to an AP application executing on a medical device or a management device.

The processor on a medical device or a management device may determine a correction bolus dosage of insulin is required by a user based on an evaluation of the number of blood glucose measurement values (415). In the example, the medical device processor may determine that a correction bolus dosage of insulin is required by a user based on an evaluation of the number of blood glucose measurement values (425). For example, the processor may be operable to access information from a data storage, which may be, for example, a memory coupled to the processor, other devices in the system, such as the sensor, a medical device, a smart accessory device, a management device, a cloud-based service, or the like. Alternatively, or in addition, the processor may be operable to calculate or derive the information useable in the determination of the correction bolus dosage. In the example, the processor may apply a function to the selected blood glucose measurement value of the number of blood glucose measurement values, the target blood glucose value of the user, and the insulin adjustment factor. At 435, the processor may obtain a final insulin value of the correction bolus dosage based on an output of the function. The final insulin value may be a volume of insulin, an amount of insulin (in units of insulin), or the like that is to be used to determine an insulin bolus dosage. For example, an insulin bolus dosage may be set based on the obtained final insulin value (445). At 455, delivery of insulin may be actuated according to the set insulin bolus dosage. For example, the processor 221 may generate a control signal that is applied to the pump mechanism 224 to expel an amount of insulin according to the set insulin bolus dosage.

Figure 5:
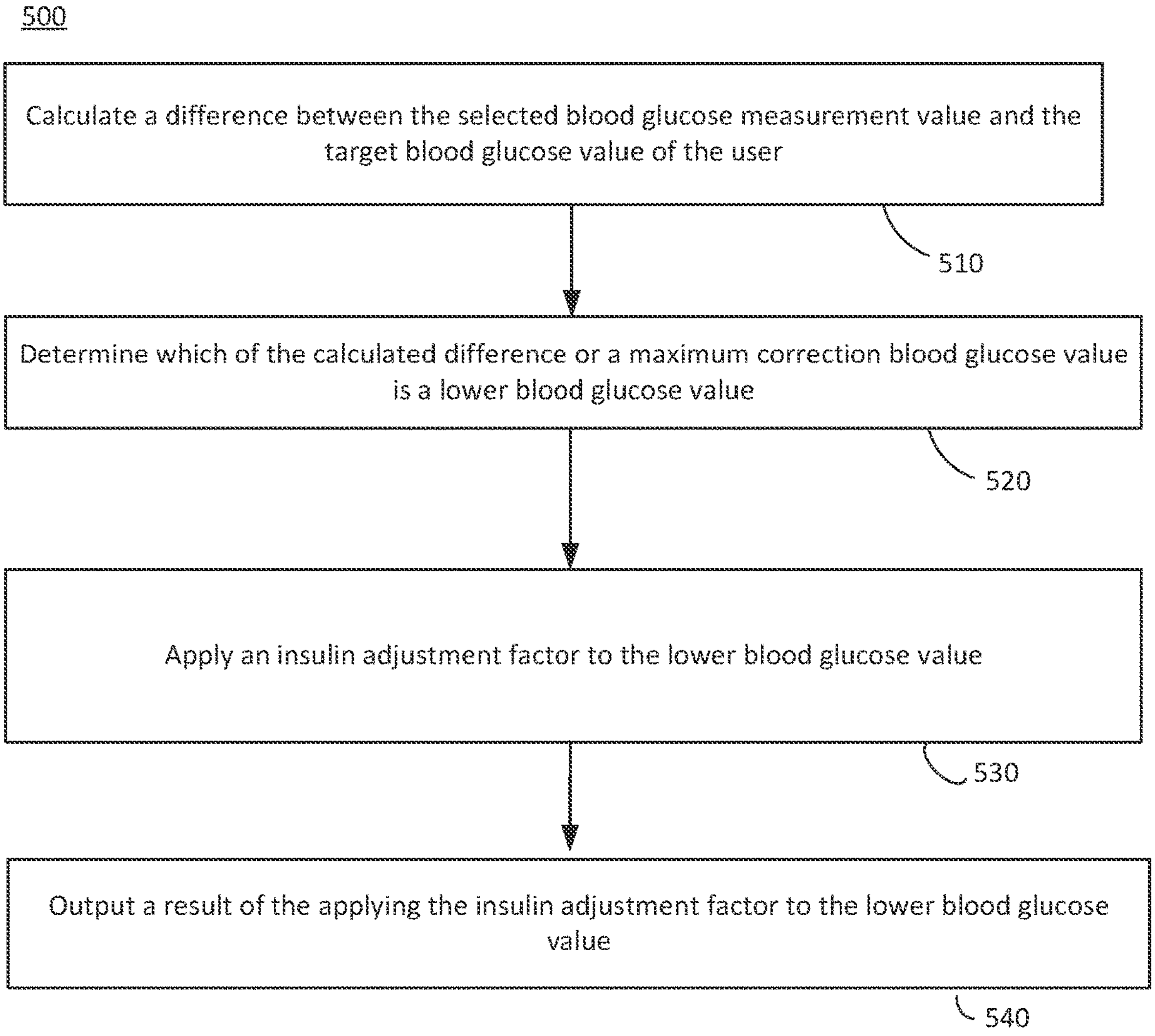
FIG. 5 illustrates a flow chart of an example subprocess for obtaining a final insulin value, such as the final insulin value of FIG. 4.

The step of obtaining a final insulin value at 435 may be performed using different process examples. FIG. 5 illustrates a flow chart of an example subprocess for obtaining the final insulin value may be completed by a processor applying a process. The process 500 may be implemented via programming code, for example, as part of the AP application, that enables a processor to calculate a difference between the selected blood glucose measurement value and the target blood glucose value of the user (510). The processor may determine which of the calculated difference or a maximum correction blood glucose value is a lower blood glucose value (520). At 530, when the lower blood glucose value is determined, an insulin adjustment factor may be applied to the lower blood glucose value. A result of the applying the insulin adjustment factor to the lower blood glucose value may be output (540).

Figure 6A:
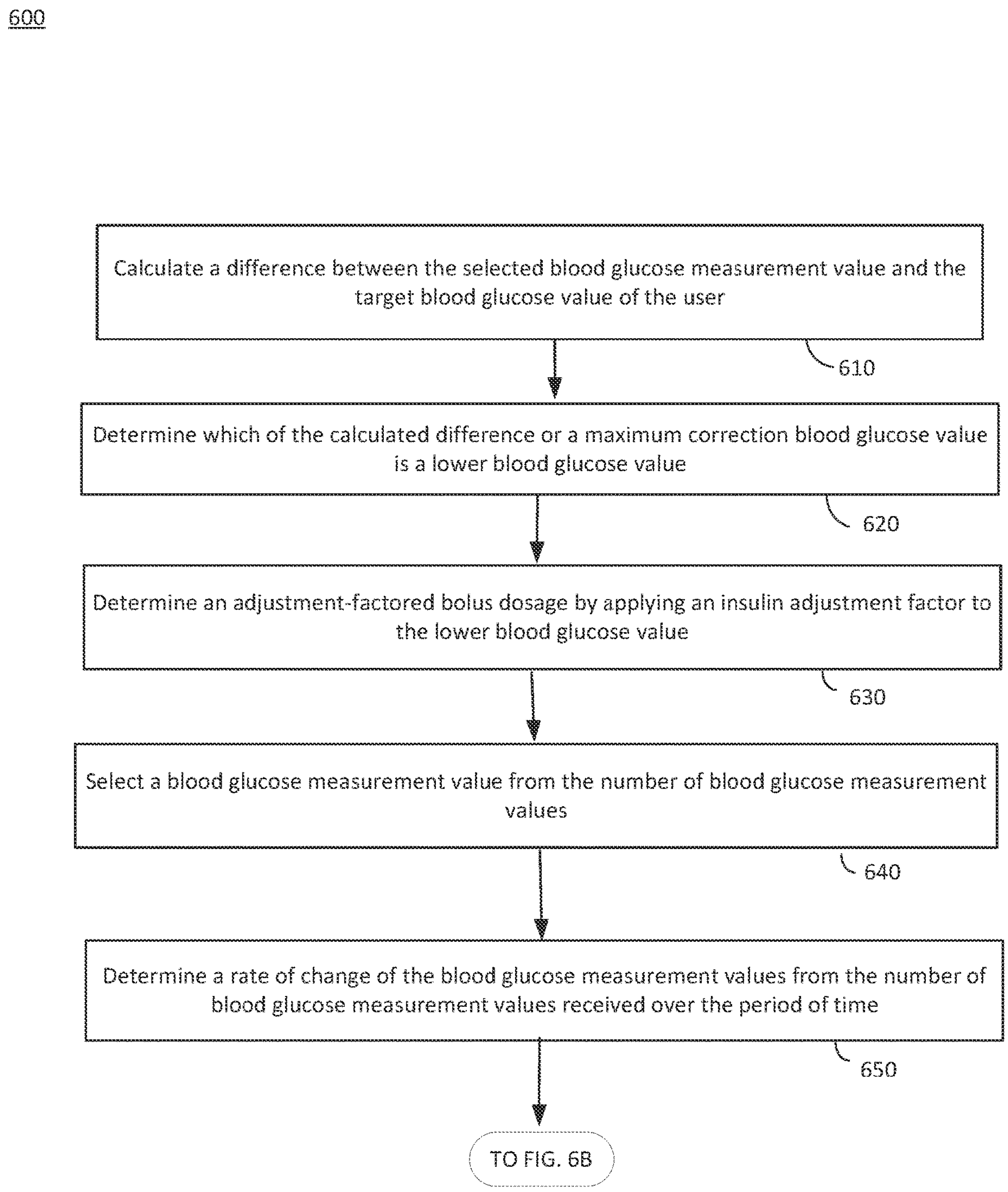
FIGS. 6A and 6B illustrate a flow chart of another example subprocess for obtaining a final insulin value.
Figure 6B:
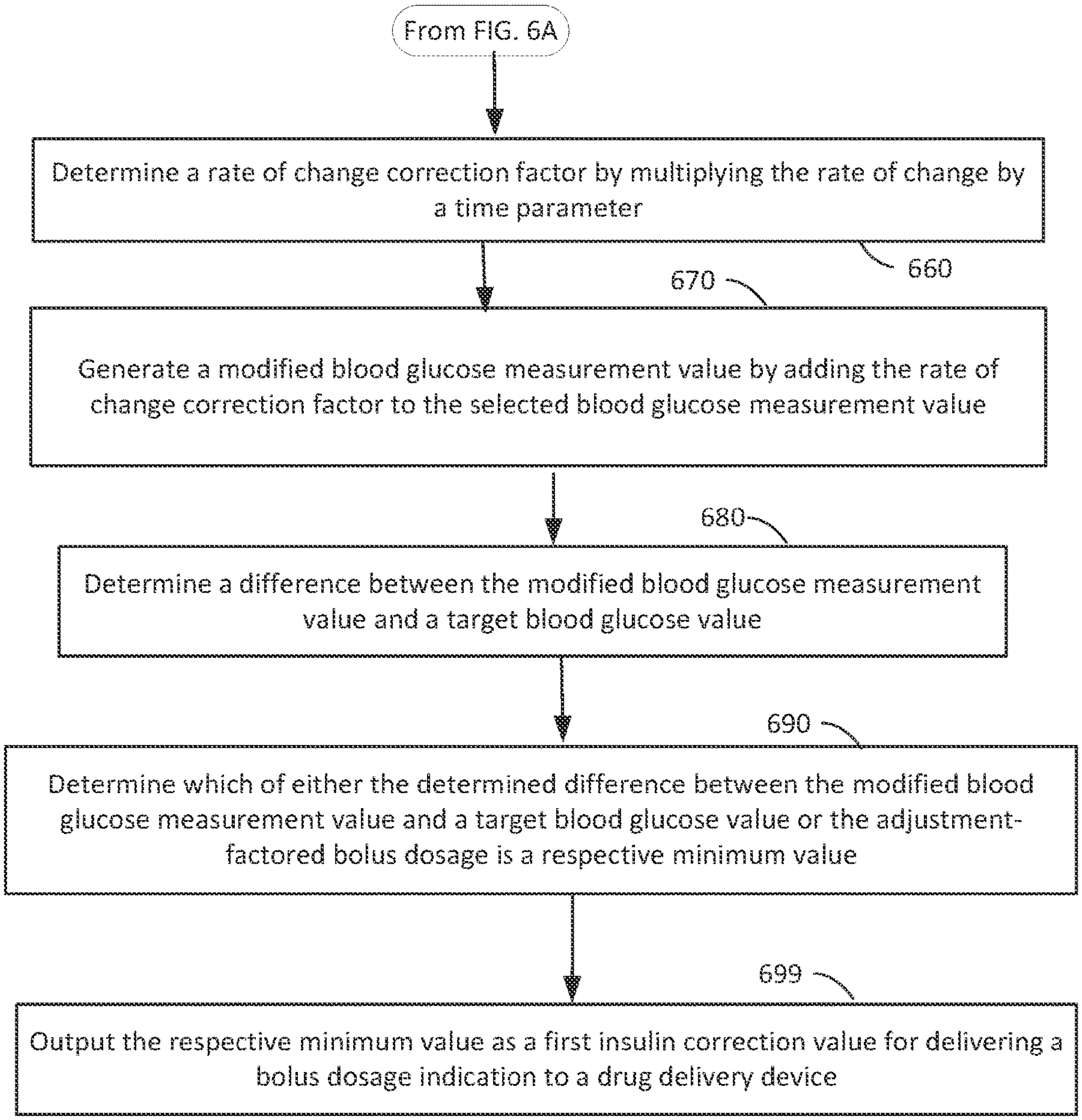

Alternatively, in another example shown in FIGS. 6A and 6B, the step of obtaining a final insulin value at 435 may be performed by a processor executing programming code that causes the processor to be operable to perform the functions of process 600. For example, at 610, the processor may calculate a difference between the selected blood glucose measurement and the target blood glucose value of the user. A determination may be made which of the calculated difference or a maximum correction blood glucose value is a lower blood glucose value (620). The maximum correction blood glucose value may be a fixed clinical medical value, such as 100 mg/dL, modifiable based on user preferences from 0 to 300 mg/dL, implied based on user's maximum bolus setting and insulin sensitivity factor clinical parameters as seen in Equation 7 below, or the like.

$$\text{Maximum Correction blood glucose} = \frac{\text{User's Maximum Bolus Setting}}{ISF} \quad \text{Eq. 7}$$

In other examples, the maximum correction blood glucose value may be specific to the particular user. For example, the maximum correction blood glucose value may be determined based on user history of administered dosages and analysis of the user's response to each respective administered dosage. The determination, at 620, may be made using a direct comparison of the respective values of the difference and the maximum correction blood glucose value, or by applying a bias weighting (e.g., a percentage such as 80/20, 60/40, a direct bias weighting, such as 0.2, or the like) to the difference, the maximum correction blood glucose value, or both.

At 630, an adjustment-factored bolus dosage may be determined by applying an insulin adjustment factor (such as IAF shown in the examples that utilize Eq. 1 or Eq. 4 above) to the lower blood glucose value determined in 620.

A blood glucose measurement value may be selected from the number of blood glucose measurement values (640). The processor may select the blood glucose measurement value based on a number of factors. For example, the selected blood glucose measurement value may be the blood glucose measurement value most recently received (i.e., the latest blood glucose measurement value) from a CGM or input into a medical device, for example, by a user, one of a blood glucose measurement value received with the past 15 minutes, 25 minutes or some other time period, or the like.

At 650, a rate of change of the blood glucose measurement values may be determined from the number of blood glucose measurement values received over the period of time. The rate of change may be determined using a number of known methods. Moving to FIG. 6B, a rate of change correction factor may be determined by multiplying the rate of change determined at 650 by a time parameter (660). Units for the rate of change of the blood glucose measurement values may be milligrams/deciliter per unit of time. A time parameter, such as T in Eq. 2, may be a time value represented in units of time such as minutes (e.g. 5, 10, 15 or 25 minutes), or the like. Of course, conversion of the time units to seconds or fractions of hours may also be used. In the example, the processor executing the programming code may generate a modified blood glucose measurement value by adding the rate of change correction factor to the selected blood glucose measurement value (670). The processor executing the programming code may determine, at 680, a difference between the modified blood glucose measurement value and a target blood glucose value. At 690, the processor executing the programming code may determine which of either the determined difference between the modified blood glucose measurement value and a target blood glucose value or the adjustment-factored bolus dosage is a respective minimum value. The processor may output the respective minimum value as a first insulin correction value for delivering a bolus dosage indication to a drug delivery device (699).

Figure 7:
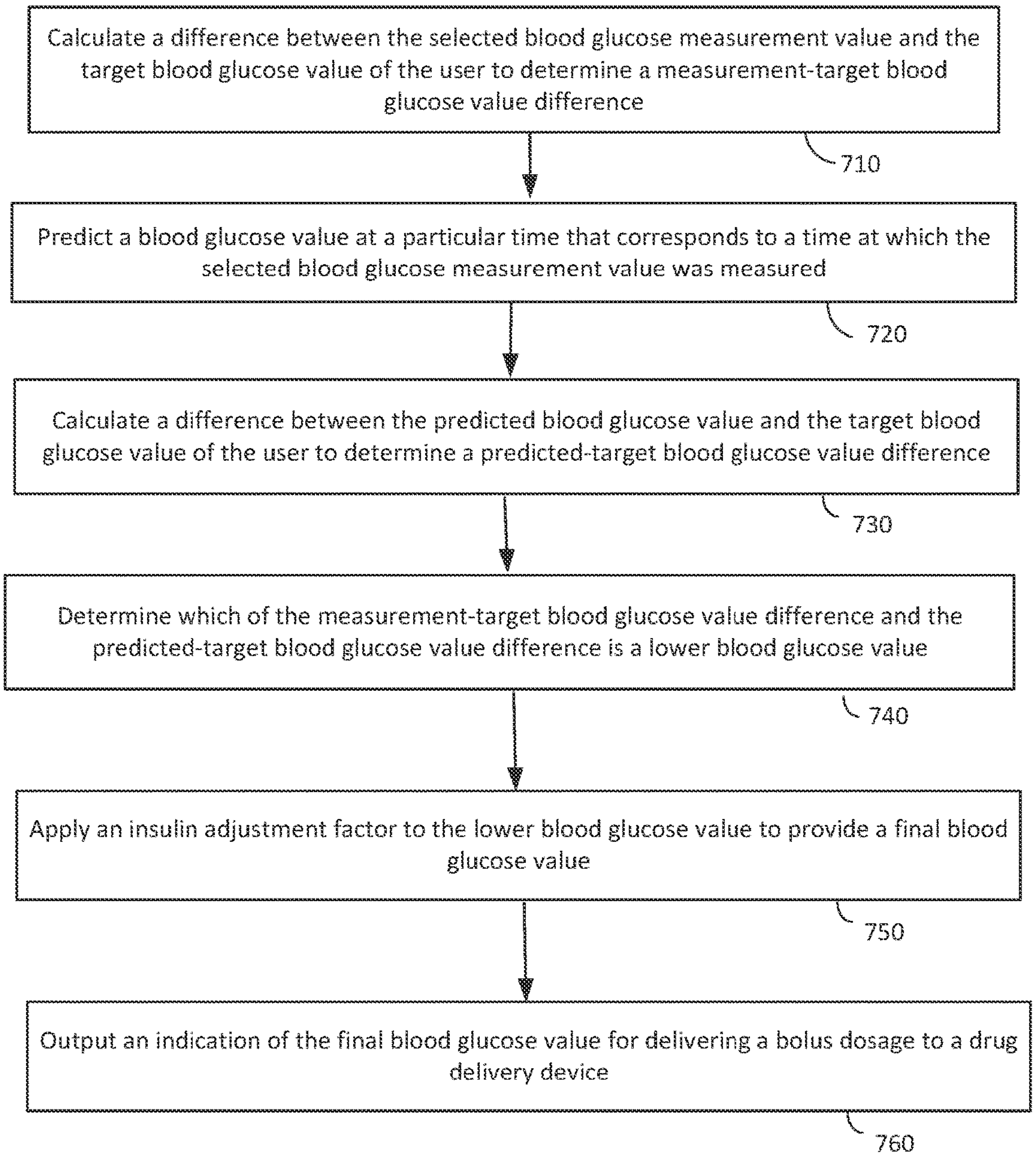
FIG. 7 illustrates a flow chart of a further example subprocess for obtaining a final insulin value.

In another alternative, FIG. 7 illustrates a flow chart of a further example subprocess for obtaining a final insulin value. As shown in the example of FIG. 7, the step of obtaining a final insulin value at 435 may be performed by a processor executing programming code that causes the processor to be operable to perform the functions of process 700. For example, at 710, the processor may calculate a difference between the selected blood glucose measurement value and the target blood glucose value of the user to determine a measurement-target blood glucose value differences. A prediction of a blood glucose value at a particular time that corresponds to a time at which the selected blood glucose measurement value was measured may be made by a processor at 720. The prediction may be based on prior user blood glucose measurements, a history of administered doses of insulin, or the like. A difference between the predicted blood glucose value and the target blood glucose value of the user may be calculated to determine a predicted-target blood glucose value difference (730). The processor executing the programming code may be operable to determine which of the measurement-target blood glucose value difference and the predicted-target blood glucose value difference is a lower blood glucose value (740). This may be determined using various methods such as a direct comparison or other process. In response to determine which the respective values is the lower blood glucose value in 740, an insulin adjustment factor may be applied to the lower blood glucose value to provide a final blood glucose value (750). For example, the lower blood glucose value may be multiplied or divided by the insulin adjustment factor or some other operation or function may apply the insulin adjustment factor to the lower blood glucose value.

In response to determining the final blood glucose value, a processor may, at 760, output an indication of the final blood glucose value for delivering a bolus dosage to a drug delivery device. The outputted indication may be used to generate a signal that is applied to a pump mechanism, such as 224 of FIG. 2, to deliver a bolus dosage to the drug delivery device.

The techniques described herein for providing safety constraints for a drug delivery system (e.g., the system 200 or any component thereof) may be implemented in hardware, software, or any combination thereof. For example, the system 200 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some embodiments, the techniques described herein, and/or any system or constituent component described herein may be implemented with a processor executing computer readable instructions stored on one or more memory components.

Some embodiments of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with embodiments of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A method, comprising:

receiving a number of blood glucose measurement values of a user over a period of time at a processor of a drug delivery device;

calculating a measurement-target blood glucose value difference between a selected blood glucose measurement value from the number of blood glucose measurement values and a target blood glucose value of the user;

calculating a predicted-target blood glucose value difference between a predicted blood glucose value and the target blood glucose value of the user;

determining which of the measurement-target blood glucose value difference or the predicted-target blood glucose value difference is a lower blood glucose value;

applying an insulin adjustment factor to the lower blood glucose value to generate an adjusted lower blood glucose value;

setting a correction bolus dosage for delivery by the drug delivery device based on the adjusted lower blood glucose value; and actuating delivery of insulin by the processor by generating a control signal to expel an amount of insulin according to the set correction bolus dosage.

2. The method of claim 1, wherein the drug delivery device is attached to skin of a body of the user via an adhesive.

3. The method of claim 1, wherein applying the insulin adjustment factor to the lower blood glucose value to generate the adjusted lower blood glucose value comprises multiplying the lower blood glucose value by the insulin adjustment factor.

4. The method of claim 1, further comprising:

selecting the insulin adjustment factor from a range of approximately 0.3 to approximately 0.7.

5. The method of claim 1, further comprising:

prior to calculating the measurement-target blood glucose value difference between the selected blood glucose measurement value and the target blood glucose value of the user, determining whether the correction bolus dosage of insulin is required for the user based on an evaluation of the number of blood glucose measurement values.

6. The method of claim 5, wherein the evaluation of the number of blood glucose measurement values comprises:

determining a trajectory of the number of blood glucose measurement values.

7. The method of claim 1, wherein setting the correction bolus dosage for delivery by the drug delivery device further comprises:

constraining the correction bolus dosage at an upper boundary by a recommended bolus dosage modified by the insulin adjustment factor.

8. The method of claim 1, further comprising:

prior to applying the insulin adjustment factor to the lower blood glucose value, setting the insulin adjustment factor to be proportional to a trajectory of the number of blood glucose measurement values.

9. The method of claim 1, further comprising:

prior to setting the correction bolus dosage, constraining the correction bolus dosage by not more than is required to meet the target blood glucose value if a trajectory of the number of blood glucose measurement values is substantially constant for a set period of time.

10. The method of claim 1, further comprising:

obtaining the predicted blood glucose value prior to calculating the predicted-target blood glucose value, wherein the predicted blood glucose value is determined using a particular time that corresponds to a time at which the selected blood glucose measurement value was measured.

11. The method of claim 1, wherein applying the insulin adjustment factor to the lower blood glucose value to generate the adjusted blood glucose value comprises dividing the lower blood glucose value by the insulin adjustment factor.

12. A non-transitory computer readable medium embodied with programming code executable by a processor, and the processor when executing the programming code is operable to perform functions, including functions to:

receive a number of blood glucose measurement values of a user over a period of time;

calculate a measurement-target blood glucose value difference between a selected blood glucose measurement value from the number of blood glucose measurement values and a target blood glucose value of the user;

calculate a predicted-target blood glucose value difference between a predicted blood glucose value and the target blood glucose value of the user;

determine which of the measurement-target blood glucose value difference or the predicted-target blood glucose value difference is a lower blood glucose value;

apply an insulin adjustment factor to the lower blood glucose value to generate an adjusted lower blood glucose value;

set a correction bolus dosage for delivery based on the adjusted lower blood glucose value; and actuate delivery of insulin by generating a control signal to expel an amount of insulin according to the set correction bolus dosage.

13. The non-transitory computer readable medium of claim 12, wherein a drug delivery device including the processor is attached to skin of a body of the user via an adhesive.

14. The non-transitory computer readable medium of claim 12, wherein the processor, when applying the insulin adjustment factor to the lower blood glucose value to generate the adjusted lower blood glucose value, is configured to:

multiply the lower blood glucose value by the insulin adjustment factor.

15. The non-transitory computer readable medium of claim 12, wherein the processor is further operable to:

select the insulin adjustment factor from a range of approximately 0.3 to approximately 0.7.

16. The non-transitory computer readable medium of claim 12, wherein the processor is further configured to:

prior to calculating the difference between the selected blood glucose measurement value from the number of blood glucose measurement values and the target blood glucose value of the user, determine whether the correction bolus dosage of insulin is required for the user.

17. The non-transitory computer readable medium of claim 12, wherein the processor is further configured to:

determine a trajectory of the number of blood glucose measurement values.

18. The non-transitory computer readable medium of claim 12, wherein the processor is further configured to:

constrain the correction bolus dosage at an upper boundary by a recommended bolus dosage modified by the insulin adjustment factor.

19. The non-transitory computer readable medium of claim 12, wherein the processor is further configured to:

set the insulin adjustment factor to be proportional to a trajectory of the number of blood glucose measurement values.

20. The non-transitory computer readable medium of claim 12, wherein the processor is further configured to:

prior to setting the insulin bolus dosage, constrain the correction bolus dosage by not more than is required to attain a current blood glucose measurement value to the target blood glucose value if a trajectory of the number of blood glucose measurement values is substantially constant for a set period of time.

* * * * *